United States Patent [19]
Uhlmann et al.

[11] Patent Number: 6,063,571
[45] Date of Patent: May 16, 2000

[54] PROCESS FOR AMPLIFYING NUCLEIC ACIDS USING DNA/PNA PRIMERS

[75] Inventors: Eugen Uhlmann, Glashütten; Gerhard Breipohl, Frankhurt, both of Germany; Steven A. Benner, Zürich, Switzerland; Michael Lutz, Offenburg, Germany

[73] Assignee: Hoechst Aktiengesellschaft, Frankfurt am Main, Germany

[21] Appl. No.: 08/927,274

[22] Filed: Sep. 11, 1997

[30] Foreign Application Priority Data

Sep. 13, 1996 [DE] Germany .................. 196 37 339

[51] Int. Cl.⁷ .................. C12Q 1/68; C12P 19/34
[52] U.S. Cl. .................. 435/6; 435/91.1; 435/91.2
[58] Field of Search .................. 432/6, 91.1, 91.2; 435/91.1, 91.2

[56] References Cited

U.S. PATENT DOCUMENTS 4,683,202  7/1987  Mullis .

FOREIGN PATENT DOCUMENTS

| 0 622 677 A2 | 11/1994 | European Pat. Off. . |
| 0 672 677 A2 | 9/1995 | European Pat. Off. . |
| 0 736 608 | 10/1996 | European Pat. Off. . |
| WO 92/20702 | 11/1992 | WIPO . |
| WO 95/08556 | 3/1995 | WIPO . |
| WO 95 16028A | 6/1995 | WIPO . |

OTHER PUBLICATIONS

Thiede, et al (1996) Nucleic Acids Res. vol. 24 (5) pp. 983–984.

Lutz, M.J., "Recognition of Uncharged Polyamide–Linked Nucleic Acid Analogs by DNA Polymerases and Reverse Transcriptases," *J. Am. Chem. Soc.* (1997) 119:3177–3178.

Eom, S.H., et al., "Structure of Taq polymerase with DNA at the polymerase active sites," *Nature* (1996) 382:278–281.

Carlsson, C., et al, "Screening for genetic mutations," *Nature* (1996) 380:207–210.

Demers, D.B., et al., "Enhanced PCR amplification of VNTR locus D1S80 using peptide nucleic acid (PNA)," *Nucl. Acids. Res.* (1995) 23:3050–3055.

Nielsen, P.E., et al., "Peptide Nucleic Acid (PNA). A DNA Mimic with a Peptide Backbone," *Bioconjugate Chem.* (1994) 5:3–7.

Perrin, K.A., et al., "Defining the Interactions between DNA and the Exonuclease Domain of DNA Polymerases," *J. Am. Chem. Soc.* (1994) 116:7427–7428.

Joyce, C.M., et al., "Function and Structure Relationships in DNA Polymerases," *Annu. Rev. Biochem.* (1994) 63:777–822.

Kong, H., et al., "Characterization of a DNA Polymerase from the Hyperthermophile Archaea *Thermococcus litoralis*," *J. Biol. Chem.* (1993) 268:1965–1975.

Reyes, R.A., et al., "Preparation of pure oligonucleotide–alkaline phosphatase conjugates," *Nucl. Acids Res.* (1993)23:5532–5533.

Egholm, M., et al., "PNA hybridizes to complementary oligonucleotides obeying the Watson–Crick hydrogen–bonding rules," *Nature* (1993) 365:566–568.

Nielsen, P.E., et al., "Sequence–Selective Recognition of DNA by Strand Displacement with a Thymine–Substituted Polyamide," *Science* (1991) 25:1497–1500.

Englisch, V.U., et al., "Chemisch modifizierte Oligonucleotide als Sonden und Agentien," *Angewandte Chemie* (1991) 103:629–646.

*Primary Examiner*—Kenneth R. Horlick
*Attorney, Agent, or Firm*—Finnegan, Henderson, Farabow, Garrett & Dunner, L.L.P.

[57] ABSTRACT

The present invention relates to a novel advantageous process for amplifying nucleic acids using DNA/PNA primers and a temperature-stable polymerase enzyme.

8 Claims, No Drawings

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: exon
      (B) LOCATION: 1..16
      (D) OTHER INFORMATION: /note= "N 16 = 5-amino-5-deoxythymidine"

(xi) SEQUENCE DESCRIPTION: SEQ ID NO: 1:

TAATACGACT CACTAN      16

(2) INFORMATION FOR SEQ ID NO: 2:

(i) SEQUENCE CHARACTERISTICS:
        (A) LENGTH: 18 base pairs
        (B) TYPE:  nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..17
        (D) OTHER INFORMATION: /note= " N1 = Acetyl-;
            N17 = ethylamino-N-(thyminylacetyl)ethanol"

(xi) SEQUENCE DESCRIPTION: SEQ ID NO: 2:

NTAATACGAC TCACTANA                                                 18

(2) INFORMATION FOR SEQ ID NO: 3:

(i) SEQUENCE CHARACTERISTICS:
        (A) LENGTH: 13 base pairs
        (B) TYPE:  nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..13
        (D) OTHER INFORMATION: /note= "N1 = Acetyl-; N13 =
            5-amino-5-deoxythymidine"

(xi) SEQUENCE DESCRIPTION: SEQ ID NO: 3:

NTGCAAGCTT AAN                                                      13

(2) INFORMATION FOR SEQ ID NO: 4:

(i) SEQUENCE CHARACTERISTICS:
        (A) LENGTH: 13 base pairs
        (B) TYPE:  nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..12
        (D) OTHER INFORMATION: /note= "N1 = Acetyl-; N11 =
            [(2-aminoethyl)-N9-adenylacetylamino]methylphosphonic
            acid"

(xi) SEQUENCE DESCRIPTION: SEQ ID NO: 4:

NTGCAAGCTT ANT                                                      13

(2) INFORMATION FOR SEQ ID NO: 5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..16

(xi) SEQUENCE DESCRIPTION: SEQ ID NO: 5:

```
TAATACGACT CACTAT                                                             16

(2) INFORMATION FOR SEQ ID NO: 6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..18

(xi) SEQUENCE DESCRIPTION: SEQ ID NO: 6:

GCCCCAGGGA GAAGGCAA                                                           18

(2) INFORMATION FOR SEQ ID NO: 7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..15

(xi) SEQUENCE DESCRIPTION: SEQ ID NO: 7:

CGAGCTTAAG TCAGC                                                              15

(2) INFORMATION FOR SEQ ID NO: 8:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..81

(xi) SEQUENCE DESCRIPTION: SEQ ID NO: 8:

GCCCCAGGGA GAAGGCAACT GGACCGAAGG CGCTTGTGGA GAAGGAGTTC ATAGCTGGGC             60

TCCCTATAGT GAGTCGTATT A                                                       81

(2) INFORMATION FOR SEQ ID NO: 9:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..46
```

(xi) SEQUENCE DESCRIPTION: SEQ ID NO: 9:

CGAGCTTAAG TCAGCGCCTA CTATAGTGAG TCGTATTAAG CTTGCA          46

PROCESS FOR AMPLIFYING NUCLEIC ACIDS USING DNA/PNA PRIMERS

DESCRIPTION

Process for amplifying nucleic acids

BACKGROUND OF THE INVENTION

The present invention relates to a novel advantageous process for amplifying nucleic acids using DNA/PNA primers and a temperature-stable polymerase enzyme.

Recently, polyamide-nucleic acid derivatives (PNAs) have been described (Michael Egholm, Peter E. Nielsen, Rolf H. Berg and Ole Buchardt, Science (1991) 254, 1497–1500; WO 92/20702; M. Egholm et al. Nature (1993) 365, 566–568; P. Nielsen, Bioconjugate Chem. (1994) 5, 3–7) which bind to complementary target sequences (DNA or RNA) with a higher affinity than natural oligonucleotides. In these so-called PNAs, the deoxyribose phosphate structure is replaced by a polyamide oligomer.

It has been found that PNAs of DNA polymerases are not accepted as primers (H. Ørum, et al., Nucl. Acids Res. (1993) 21, 5332–5336; D. B. Demers, et al., Nucl. Acids Res. (1995) 23, 3050–5) and thus cannot be used as primers for amplifying nucleic acids with the aid of DNA polymerases.

In EP-A 0672 677 and WO 95/08556, PNA/DNA hybrid molecules are described which can also be employed, inter alia, as primers for amplifying nucleic acids using Klenow polymerases.

An advantage of the use of PNA/DNA primers instead of natural oligonucleotide primers for amplifying nucleic acids is that the nucleic acid strand copied with the aid of the PNA primer contains, at the 5' end, a PNA moiety which is stable to 5'-exonucleases. All natural DNA and RNA sequences in the reaction mixture can thus be degraded by 5'-exonucleases without the PNA-containing strand being attacked. However, the polymerase reactions with Klenow polymerase enzymes described in WO 95/08556 only succeed if the PNA/DNA primers described therein have at least four nucleotides at the 3' terminus, while a PNA/DNA primer with only two nucleotides at the 3' terminus fails in the DNA polymerase reaction.

It is known from EP-A 0672 677 that PNA/DNA hybrids with only one 5'-deoxy-5'-aminonucleoside at the carboxyl terminus can be employed as primers if the DNA polymerase of *E. coli* (Klenow fragment) is employed for the enzymatic polymerization.

These results are completely unexpected, since it is evident from crystal structure studies on DNA polymerase/primer-template complexes that interactions between the phosphodiester functions of the primer and the enzyme exist in several positions (C. M. Joyce, T. A. Steitz, Annu. Rev. Biochem. (1994) 63, 777–822; S. H. Eom, Nature (1996) 382, 278–281).

The fact that the elimination of the negative charges in the primer counteracts the acceptance of the primer by polymerases was additionally confirmed by investigations with primers in which the natural phosphodiester functions were partially replaced by neutral internucleoside bridges, such as, for example, 3'-O-sulfonate or 3'-N-sulfonamide (K. A. Perrin et al., J. Am. Chem. Soc. (1994) 116, 7427–7428).

On the basis of these results, it was to be assumed that with respect to its partial acceptance of uncharged primers, the Klenow enzyme, which is constituted by the PNA/DNA hybrid molecules described in EP-A 0672 677 and with a 5'-deoxy-5'-aminonucleoside at the carboxyl terminus, is an exception among the various DNA polymerases.

A disadvantage of the use of the Klenow polymerase for amplifying nucleic acids using PNA/DNA primers is that this enzyme is not sufficiently temperature-stable that, for example, an amplification of the template strand copied can be achieved analogously to known amplification techniques such as PCR and LCR.

The object of the present invention was therefore to find other DNA polymerases which elongate PNA/DNA primers without having the abovementioned disadvantages.

Surprisingly, it has now been found that temperature-stable DNA polymerases can elongate PNA/DNA primers which, at one end, carry at least one, optionally modified, nucleoside unit with a 3'-hydroxyl group.

DETAILED DESCRIPTION OF THE INVENTION

The present invention thus relates to a process for amplifying nucleic acids with the aid of a polymerase enzyme and of one or more PNA/DNA primers which, at one end, have at least one nucleoside unit with a 3'-hydroxyl group, and of the components customarily needed for amplifying nucleic acids, such as, for example, unlabeled or radiolabeled deoxyribonucleotide triphosphates, wherein the polymerase enzyme is temperature-stable.

For example, the TTH™ DNA polymerase from Thermus spec., the Pwo DNA polymerase from *Pyrococcus woesei*, the 9° N DNA polymerase™ from Thermococcus sp. strain 9° N or the VENT™ polymerase from *Thermococcus litoralis* are suitable.

Another embodiment of the invention is that more than one type of polymerase is used in the process. For example a combination of two or more different types of polymerases can be used therefore. One special embodiment of the invention is that a combination of VENT™ DNA polymerase and TTH™ DNA polymerase is used.

Examples of suitable PNA/DNA primers are described in EP 0 622 677 A2. In particular, the PNA/DNA primers described in EP 0 622 677 A2 are suitable if they have one to three, preferably one, nucleoside unit(s) at one end.

Those PNA/DNA primers in which the nucleoside units are found at the 3' end of the PNA/DNA primer are also preferred.

Suitable PNA/DNA primers, for example, are those of the formula I formula I

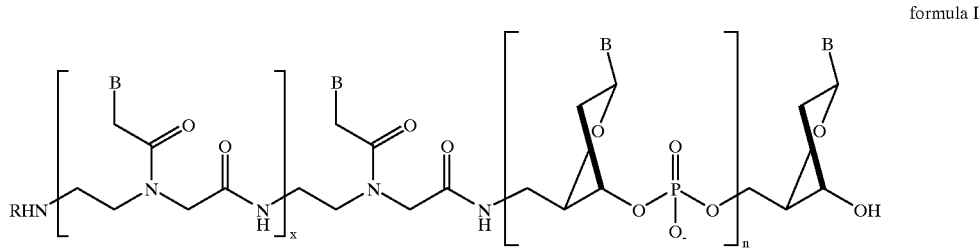

in which
n is 0–2,
x is 2–50 and
R is hydrogen or an organic radical having 2–18 carbon atoms, and
B independently of one another is a base customary in nucleotide chemistry, for example a natural base such as adenine, cytosine, thymine, guanine, uracil, hypoxanthine or an unnatural base such as, for example, purine, 2,6-diaminopurine, 7-deazaguanine, 7-deazaadenine, $N^4N^4$-ethanocytosine, $N^6N^6$-ethano-2,6-diaminopurine, pseudoisocytosine, 5-methylcytosine, 5-fluorouracil, 5-($C_3$–$C_6$)-alkynyluracil, 5-($C_3$–$C_6$)-alkynylcytosine or their prodrug forms.

Suitable DNA/PNA primers are additionally those of the formula II or III

The term nucleoside unit is understood as meaning a nucleoside which has a sugar radical and a base, it being possible for the base and the sugar radical to be modified, and the individual nucleoside units being linked to one another via a phosphate radical, and furthermore the nucleoside units being linked to the PNA moiety of the primer via a phosphate radical or an amide bond. The sugar radical is customarily a ribose radical, although it is also possible for this to be modified.

Examples of nucleosides which have modifications on the sugar radical are: 5'-amino-5'-deoxythymidine, ethylamino-N-(thyminylacetyl)ethanol, [(2-aminoethyl)-N9-adenylacetylamino]methylphosphonic acid.

Bases are understood as meaning customary bases such as, for example, the natural bases adenine, cytosine, thymine, guanine, uracil, hypoxanthine or else alternatively unnatural bases such as, for example, purine, 2,6-diaminopurine, 7-deazaguanine, 7-deazaadenine, $N^4N^4$- formula II

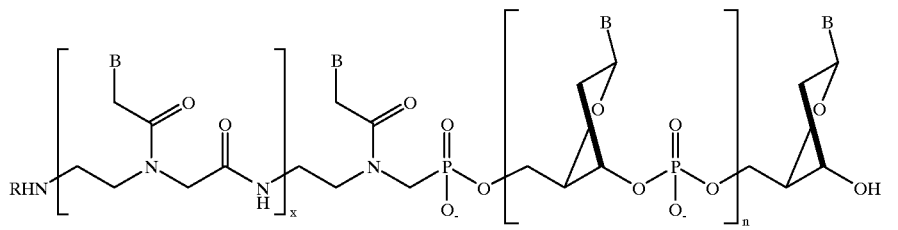

formula III

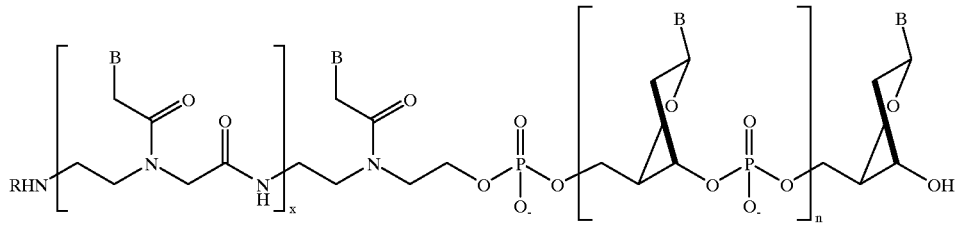

n is 0–2
x 2–50 and
R is hydrogen or an organic radical having 2–18 carbon atoms, and B has the abovementioned meaning.

Preferred DNA/PNA primers are those of the formula I, II or III in which n=0. Preferred DNA/PNA primers are also those of the formula I, II or III in which x is 5-25, particularly preferably 10-18.

Examples of an organic radical having 2–18 carbon atoms are $C_2$–$C_{18}$-alkanoyl, preferably $C_2$–$C_{10}$-alkanoyl, particularly preferably acetyl, $C_2$–$C_{18}$-alkyl, preferably $C_2$–$C_{10}$-alkyl, $C_3$–$C_8$-cycloalkanoyl or $C_3$–$C_{13}$-heteroaryl.

ethanocytosine, $N^6N^6$-ethano-2,6-diaminopurine, pseudoisocytosine, 5-methylcytosine, 5-fluorouracil, 5-($C_3$–$C_6$)-alkynyluracil, 5-($C_3$–$C_6$)-alkynylcytosine or their prodrug forms.

Temperature-stable polymerase enzymes are understood as meaning enzymes which allow amplification of nucleic acids such as, for example, DNA or RNA, preferably DNA, without the enzyme having to be made available again for further copying processes after the necessary thermal strand separation.

In contrast to the Klenow enzyme, which only allows a single copying process of the template strand because it is deactivated in the subsequent thermal strand separation, it is possible, using a temperature-stable polymerase such as, for example, the VENT™ polymerase and excess PNA/DNA primer, for an amplification of the copied template strand to be achieved analogously to known amplification techniques such as, for example, PCR (polymerase chain reaction) and LCR (ligase chain reaction) (for PCR see, for example, Methods in Molecular Biology: 15, (1993) PCR Protocols; edited by B. A. White, Humana Press).

The elongation of the PNA/DNA primer with the aid of thermostable DNA polymerases is particularly highly suitable for the preparation of multiple copies of the template, the amplification product preferably containing radioactive or nonradioactive labeling groups. For example, for the preparation of radiolabeled amplificates, [$\alpha$-$^{32}$P]- or [$\alpha$-$^{35}$S]-deoxynucleoside-5'-triphosphate can be employed in the polymerase reaction. In a similar manner, by incorporation of nucleoside triphosphates which contain nonradioactive labeling groups, corresponding nonradiolabeled DNA fragments are accessible by methods known per se (U. Englisch and D. Gauss (1991) Angew. Chem., 103, 629–46).

The amplification reaction is carried out, for example, according to the following scheme.

Primer/amplification reaction scheme (linear PCR):

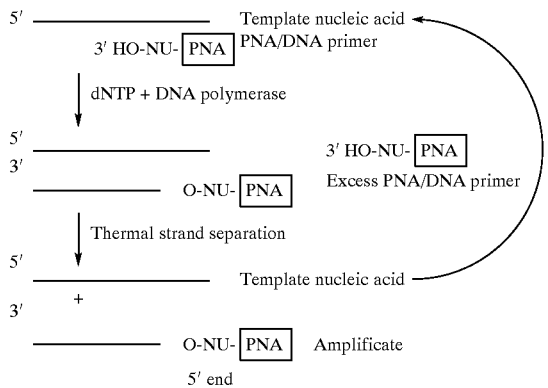

NU=Nucleoside unit(s)
dNTP=deoxynucleotide triphosphate

According to PCR techniques known to the person skilled in the art, it is possible, with the aid of the PNA/DNA primers described, for an exponential amplification of suitable template nucleic acids, in particular of template DNA, to be carried out.

Compared with the pure PNAS, which cannot exert a primer function, the use of the PNA/DNA primers in combination with temperature-stable enzymes such as the VENT™ polymerase has the further advantage that the originally laborious and less sensitive detection by means of capillary electrophoresis (C. Carlson et al., Nature (1996) 380, 207) is superseded by more rapid and more sensitive detection methods, such as, for example, autoradiography, PHOSPHORUS IMAGER™ or antibody methods.

The present invention extends very generally to the use in diagnosis, in particular in diagnosis of diseases that are associated with expression of one or more genes such as those associated with pathological conditions. The process can be used to detect the presence, the absence or the amount of the target nucleic acid sequences to which they bind.

The invention further extends to the use of the process in diagnostic tests.

The process of the present invention can be used, for example, for the diagnosis of infections or diseases caused by viruses, for example by HIV, HSV-1, HSV-2, influenza, VSV, hepatitis B or papilloma viruses.

The process of the present invention can also be used, for example, for the diagnosis of cancer. In this connection, for example, the used targets are involved in the development of cancer or the growth of cancers. Examples of such targets are:
1) nuclear oncoproteins such as, for example, c-myc, N-myc, c-myb, c-fos, c-fos/jun, PCNA, p120;
2) cytoplasmic/membrane-associated oncoproteins such as, for example, EJ-ras, c-Ha-ras, N-ras, rrg, bcl-2, cdc-2, c-raf-1, c-mos, c-src, c-abl;
3) cellular receptors such as, for example, the EGF receptor, c-erbA, retinoid receptors, protein kinase regulatory subunit, c-fms;
4) cytokines, growth factors, extracellular matrix such as, for example, CSF-1, IL-6, IL-1a, IL-1b, IL-2, IL4, bFGF, myeloblastin, fibronectin.

The process of the present invention is furthermore suitable, for example, for the diagnosis of diseases which are influenced by integrins or cell-cell adhesion receptors, for example by VLA4, VLA-2, ICAM, VCAM or ELAM.

The process of the present invention is also suitable, for example, for the diagnosis of diseases which are influenced by proliferation and/or migration of cells. Then for example, targets can be used which are involved in proliferation and/or migration processes. Examples of such targets are:
1) nuclear transactivator proteins and cyclins such as, for example, c-myc, c-myb, c-fos, c-fos/jun, cyclins and cdc2 kinase;
2) mitogens or growth factors such as, for example, PDGF, bFGF, EGF, HB-EGF, VEGF and TGF-β;
3) cellular receptors such as, for example, bFGF receptor, EGF receptor, VEGF receptor and PDGF receptor.

The VENT™ polymerase has a 3'→5' exonuclease activity which degrades normal DNA primer (Kong et al., J. Biol. Chem. (1993) 1965–1975). The primers according to the invention have an increased stability to this nucleolytic degradation.

Experiments with a large number of known, commercially available DNA polymerases, then, showed that, for example, the temperature-stable TTH™ DNA polymerase from Thermus spec., the Pwo DNA polymerase from Pyrococcus woesei, the 9° N DNA polymerase™ from Thermococcus sp. strain 9° N or the VENT™ polymerase from *Thermococcus litoralis* are able to elongate a PNA/DNA primer which; at one end, carries at least one nucleoside unit with a 3'-hydroxyl group.

The use of the VENT™ polymerase is advantageous, as reactions with VENT™ polymerase produce copies of nucleic acid fragments of full length.

The use of the TTH™ DNA polymerase is additionally advantageous, as a high amplification rate is achieved.

For the process according to the invention, it is advantageous if the DNA/PNA primer is present in an excess with respect to the template. A 2- to 20-fold excess of DNA/PNA primer is advantageous and a 5- to 10-fold excess is particularly advantageous (in each case based on the molecular weight).

Sequences of the PNA/DNA primers, DNA primers and DNA templates:
PNA/DNA primer 1 (SEQ. ID NO. 1):
H-taa tac gac tca cta-(5'NH-T)-3'
(5'NH-T is 5'-amino-5'-deoxythymidine, for structure see formula I, n=0)
PNA/DNA primer 2 (SEQ. ID NO. 2):
Acetyl-taa tac gac tca cta-(eae(t) A-3'
(eae(t) is the ethylamino-N-(thyminylacetyl)ethanol unit, for structure see formula III, n=0)

PNA/DNA primer 3 (SEQ. ID NO. 3):
Acetyl-tgc aag ctt aa (5'NH-T)-3'
(5'NH-T is 5'-amino-5'-deoxythymidine, for structure see formula I, n=0)
PNA/DNA primer 4 (SEQ. ID NO. 4):
Acetyl-tgc aag ctt a (PHONA-a) (T)-3'
(PHONA-a is the [(2-aminoethyl)-N9-adenylacetylamino] methylphosphonic acid unit, for structure see formula II, n=0)
DNA primer 1 (SEQ. ID NO. 5):
5'-d(TM TAC GAC TCA CTA T-3')
DNA primer 2 (SEQ. ID NO. 6):
5'-d(GCC CCA GGG AGA AGG CAA-3')
DNA primer 3 (SEQ. ID NO. 7):
5'-d(CGAGCTTMGTCAGC-3')
DNA template 3 (81-mer) (SEQ. ID NO. 8):
5'-d(GCC CCA GGG AGA AGG CM CTG GAC CGA AGG CGC TTG TGG AGA AGG AGT TCA TAG CTG GGC TCC CTA TAG TGA GTC GTA TTA-3')
DNA template 4 (46-mer) (SEQ. ID NO. 9):
5'-d(CGA GCT TM GTC AGC GCC TAC TAT AGT GAG TCG TAT TM GCT TGC A-3')
Capital letters: DNA
Small letters: PNA

EXAMPLES

Example 1

Preparation of the nucleic acid substrates PNA/DNA primer 1, DNA primers 1 to 3 and DNA templates 3 and 4

The PNA/DNA primer 1 (16-mer, H-taatacgactcacta (5'NH-T)-3') was synthesized as described in EP 0672 677 A2. The DNA primers 1, 2 and 3 and the DNA templates 3 and 4 were synthesized on an ABI synthesizer and purified by polyacrylamide gel electrophoresis. The DNA primer 1 (15 pmol) was labeled at the 5' end using 10 units of T4 polynucleotide kinase (Gibco BRL) in a total volume of 60 μl using 10 mCi of Redivue [γ-$^{32}$P]ATP (Amersham, 3000 Ci/mmol). Phosphorylation was carried out by incubation at 37° C. for 90 min. The reaction was then stopped by heating at 85° C. for 15 minutes.

Example 2

Elongation of PNA/DNA primers with the aid of the thermostable DNA polymerases VENT™ polymerase and TTH™ DNA polymerase (filling-in reactions)

In order to ensure complete binding of the primer to the template for the filling-in reaction, the hybridization of the primer on the template was carried out in a total volume of 500 μl, containing 1.8 mM tris HCl (pH 7.0), 0.5 mM MgCl$_2$ and 23 mM NaCl, using 15 pmol of primer (either labeled DNA primer 1 or unlabeled DNA/PNA primer 1) and 50 pmol of DNA template 3. This mixture was heated at 95° C. for 15 min and then cooled to room temperature for 1 h. TTH™ DNA polymerase and VENT™ polymerase are obtainable from Boehringer Mannheim and New England Biolabs. The enzymatic reactions were carried out in a total volume of 25 μl in a suitable buffer using 0.15 pmol of primer/template complex and all dNTPs needed in a final concentration of a) 5 mM and b) 50 mM. In the case of the PNA/DNA primer 1, unlabeled dCTP was replaced by [α-$^{32}$P]-dCTP (400 Ci/mmol). If MgCl$_2$ or MgSO$_4$ was necessary for the enzymatic reaction, the compound was added to the reaction mixture in a final concentration of 2 mM. The reaction was started by addition of the enzyme and the mixture was incubated either at 37° C. or at 75° C. for 15 min. The reaction was then interrupted by addition of 5 μl of a stop/loading dye (New England Biolabs). Aliquot parts of each reaction (5 μl) were analyzed by means of polyacrylamide gel electrophoresis on native gel (gel strength 12%, 10 watts for 4 h) and denatured gel (gel strength 15%, 35 watts for 2 h). The gels were then fixed in an aqueous solution of 12% (v/v) methanol and 10% (v/v) acetic acid, dried and investigated by means of autoradiography by overnight exposure of a PHOSPHORUS IMAGER™ plate (Molecular Dynamics).

Example 3

Linear PCR reactions (amplification)

For amplification of the template strand with the aid of the VENT™ DNA polymerase and of the PNA/DNA primer 1, an excess of primer of 20 pmol of PNA/DNA primer 1 was mixed with 2 pmol of DNA template 3 (81 -mer) and 200 mM dNTPs in a final volume of 50 μl of suitable reaction buffer. The mixture was covered with a layer of mineral oil and the reaction was started by addition of 2 units of VENT™ DNA polymerase. The polymerase reaction was carried out in the following manner: 30 cycles 1 min 94° C., 2 min 58° C., 50 sec 72° C. and finally, to complete the reaction, 8 min at 72° C. The mixture was extracted once with phenol, then with phenol/chloroform and finally with chloroform. The DNA was precipitated using 7.8 M ammonium acetate and 100% (v/v) ethanol. The precipitate was dissolved in 10 μl of TE buffer and an aliquot was analyzed with the aid of gel electrophoresis.

Example 4

N-(2-Monomethoxytritylamino)ethylaminoethanol

A solution of 9.24 g of monomethoxytrityl chloride in 60 ml of dichloromethane is added in the course of 2 hours to a stirred solution of 9.3 g of N-(2-hydroxyethyl) diaminoethane in 100 ml of anhydrous dimethylformamide at 0° C.

The mixture is stirred overnight at 4° C. The solvent is then removed in vacuo, and the residue is partitioned between 100 ml of ethyl acetate and 50 ml of water. The aqueous phase is evaporated four times with 40 ml ethyl acetate. The residual crude product is purified by means of chromatography on silica gel using a gradient of (1–10%) methanol in ethyl acetate which contains 1% triethylamine. The fractions containing the pure product are combined and evaporated to dryness.

Yield: 7.91 g of foam.

R$_f$: 0.14 (ethyl acetate/methanol/triethylamine: 100/10/1)

MS(FAB, MeOH/NBA/LiCl): 383.3 (M+Li)+

Example 5

N-2-(Monomethoxytritylamino)ethylamino-N-(thyminylacetyl)ethanol 1.84 g of carboxymethylthymine are dissolved in 50 ml of anhydrous dimethylformamide, then 3.24 g of TOTU and 3.4 ml of diisopropyl-ethylamine are added. The mixture is stirred for 20 minutes, and 3.76 g of N-(2-monomethoxytritylamino)ethylaminoethanol from Example 4 are then added. The solution is stirred at room temperature for 16 hours and then evaporated in vacuo. The residue is dissolved in 80 ml of ethyl acetate and then extracted four times with 20 ml of water in which 0.5% triethylamine is contained. The organic phase is dried over sodium sulfate and concentrated to approximately 15 ml. The product is precipitated by dropwise addition to 200 ml of diethyl ether with stirring. The crude product is filtered off and dried. The product is further purified by means of chromatography on silica gel using a gradient of (2–5%) methanol in ethyl acetate/heptane (10/1) in which 1% triethylamine is contained. The fractions containing the pure product are combined and evaporated to dryness, and the residue is triturated with diethyl ether.

Yield: 1.95 g of amorphous solid.

$R_f$: 0.46 (ethyl acetate/methanol/triethylamine: 100/20/1)

MS(ES$^+$): 543.3 (M+H)$^+$

Example 6

2-Cyanoethyl 2-(2-[(4-methoxyphenyl) diphenylmethyl]aminoethyl)-[(5-methyl-2,4-dioxo-3, 4-dihydro-2H-pyrimidin-1-yl)acetyl]aminoethyl diisopropylphosphoramidate N-(2-Hydroxyethyl)-N-(2-[(4-methoxyphenyl) diphenylmethyl]aminoethyl)-2-(5-methyl-2,4-dioxo-3,4-dihydro-2H-pyrimidin-1-yl)acetamide from Example 5 (0.5 g; 0.922 mmol) is dissolved in anhydrous dichloromethane (15 ml). N,N-Diisopropylethylamine (3.69 mmol; 0.63 ml) and 2-cyanoethyl-N,N-diisopropylchlorophosphoramidite (1.10 mmol; 0.24 ml) are added to this solution. After one hour, ethyl acetate is added to the reaction mixture, and the solvent is evaporated in vacuo. The residue is dissolved in ethyl acetate and the solution is washed four times with saturated aqueous NaCl solution. The organic phase is dried (Na$_2$SO$_4$), filtered and evaporated in vacuo. The residue is purified by means of column chromatography on silica gel using dichloromethane:ethyl acetate:NEt$_3$ (49.5:49.5:1) as eluent. The product-containing fractions are combined and concentrated; the compound mentioned in the heading is obtained as a white solid in a yield of 0.474 g (69%).

$R_f$=0.45 (dichloromethane:ethyl acetate/1:1); $^{31}$P NMR (CDCl$_3$) d 133.75 (s), 134.5 (s).

MS (FAB): 743.4 (M$^+$)

Example 7

PNA/DNA primer 2, acetyl-taa tac gac tca cta-(eae (t) A-3'

A synthesis column packed with commercially available adenosine-derivatized glass of controlled pore size (5 mmol) is mounted on an Eppendorf Biotronik Ecosyn D 300 DNA synthesizer, and the 5'-terminal dimethoxytrityl group is removed by treatment with a 3% strength trichloroacetic acid solution in dichloromethane. After thorough washing with acetonitrile, a 0.1 M solution of ethylamino-N-(thyminylacetyl)ethanol phosphoramidite mixed with a DNA activator solution (tetrazole in acetonitrile, Applied Biosystems) is added to the column. The coupling reaction is allowed to run for 15 minutes, then it is repeated. The column is washed with acetonitrile, then DNA oxidation solution (iodine, pyridine, water; Applied Biosystems) is added to the column for one minute. After washing, the unreacted hydroxyl functions are protected by capping with acetic anhydride, N-methylimidazole and lutidine in THF (Applied Biosystems). After thorough washing with acetonitrile, the N-monomethoxytrityl protective group is removed by treatment with a 3% strength trichloroacetic acid solution in dichloromethane. The PNA synthesis is then continued as described in EP 0672 677 A2. After conclusion of the synthesis, the N-terminal monomethoxytrityl protective group is removed by treatment with a 3% strength trichloroacetic acid solution in dichloromethane, and the amino terminus is protected by capping with acetic anhydride, N-methylimidazole and lutidine in THF (Applied Biosystems). The primer is cleaved from the solid substrate with the aid of concentrated aqueous ammonia solution, and the basic protective groups are removed by heating this solution to 55° C. for 5 hours. Some of the sample is purified by means of semipreparative C$_{18}$ reverse-phase HPLC using 10–80% MeCN in 0.1 M triethylammonium acetate as an eluent. After desalting on a Sephadex NAP-10 column (Pharmacia) and lyophilization, the PNA/DNA primer 2 is obtained in a yield of 2 OD$_{260}$ (=10.38 nmol). MS (MALDITOF) m/z 4636.1 (calculated 4635.41).

Example 8

PNA/DNA primer 3, acetyl-tgc aag ctt aa (5'NH—T)—OH 3'

PNA/DNA primer 3 (12-mer, acetyl-tgc aag ctt aa (5'NH—T)—OH 3') is synthesized analogously to PNA/DNA primer 1, as described in EP 0672 677 A2. After the removal of the monomethoxytrityl group of the last PNA unit, however,capping is performed as described in Example 7.

Example 9:

PNA/DNA primer 4, acetyl-tgc aag ctt a (PHONA-a) (T)—OH-3'

PNA/DNA primer 4 is synthesized starting from the CPG substrate loaded with thymidine. The dimethoxytrityl group is removed by treatment with a 3% strength trichloroacetic acid solution in dichloromethane. The PHONA-a monomer unit is prepared as described in EP 0739898 and coupled to the hydroxyl group. The PNA synthesis is then continued as described in EP 0672 677 A2.

Example 10

Filling-in reaction using PNA/DNA primer 1, 81-mer DNA template 3 and Pwo DNA polymerase (*Pyrococcus woesel*)

The PNA/DNA primer 1 (15 pmol) was hybridized with the DNA template 3 (50 pmol) in a total volume of 500 µl, in which 1.8 mM tris HCl (pH 7.0), 0.5 mM MgCl$_2$ and 23 mM NaCl were contained. The filling-in reactions were carried out in the buffer (25 µl) prepared for Pwo DNA polymerase, which contained 0.15 pmol of primer/template complex and all dNTPs necessary in a final concentration of 50 µmol. Nonlabeled dCTP was replaced by [α-$^{32}$P]-dCTP (400 Ci/mmol). The reaction was initiated by addition of 2 units of Pwo DNA polymerase (*Pyrococcus woesei*) (supplier: Boehringer Mannheim, Germany) and incubated at 75° C. for 15 minutes. Aliquot parts of each reaction (5 µl) were analyzed both by native (12% acrylamide, 10 watts, 4 hours) and, after heating to 95° C. for 20 minutes, by denatured (15% acrylamide, 35 watts, 2 hours) PAGE (polyacrylamide gel electrophoresis). The gels were fixed, dried and subjected to autoradiography (PHOSPHORUS IMAGER™, Molecular Dynamics).

Example 11

Filling-in reaction using PNA/DNA primer 1, 81-mer DNA template 3 and 9°N DNA polymerase™

The filling-in reaction is carried out as described in Example 10, but 9°N DNA polymerase (New England Biolabs) is employed in the appropriate buffer.

Example 12

Filling-in reaction using PNA/DNA primer 2, 81-mer DNA template 3 and Pwo DNA polymerase (*Pyrococcus woesei*)

The filling-in reaction is carried out analogously to Example 10, but PNA/DNA primer 2 is employed.

Example 13

Filling-in reaction using PNA/DNA primer 2, 81-mer DNA template 3 and 9°N DNA polymerase™

The filling-in reaction is carried out analogously to Example 11, but PNA/DNA primer 2 is employed.

Example 14

Polymerase chain reaction (PCR) using PNA/DNA primer 3, DNA primer 3, 46-mer DNA template 4 and TTH™ DNA polymerase For the PCR, 50 pmol of PNA/DNA primer 3 from Example 8, 5 pmol of DNA template 4, 0.5 pmol of 5'-labeled DNA primer 3 and 200 µM dNTPs are mixed in a final volume of 50 µl, in which the TTH™ DNA polymerase reaction buffer and 2 units of TTH™ DNA polymerase are contained. The other conditions are as described in Example 10. The amplification is carried out as follows: 30 cycles, 1 minute 94° C., 2 minutes 58° C., 50 seconds 72° C.

Example 15

Polymerase chain reaction (PCR) using PNA/DNA primer 4, DNA primer 3, 46-mer DNA template 4 and TTH™ DNA polymerase For the PCR, 50 pmol of PNA/DNA primer 4 from Example 9, 5 pmol of DNA template 4, 0.5 pmol of 5'-labeled DNA primer 3 and 200 µM dNTPs are mixed in a final volume of 50 µl, in which the TTH™ DNA polymerase reaction buffer and 2 units of TTH™ DNA polymerase are contained. The other conditions are as described in Example 10. The amplification is carried out as follows: 30 cycles, 1 minute 94° C., 2 minutes 58° C., 50 seconds 72° C.

Example 16

Polymerase chain reaction (PCR) using PNA/DNA primer 1, 81-mer DNA template 3 and TTH™ DNA polymerase For the PCR, 50 pmol of PNA/DNA primer 1 from Example 1, 5 pmol of DNA template 3 (see Example 1), 0.5 pmol of 5'-labeled DNA primer 2 and 200 µM dNTPs are mixed in a final volume of 50 µl, in which the TTH™ DNA polymerase reaction buffer and 2 units of TTH™ DNA polymerase are contained. The other conditions are as described in Example 10. The amplification is carried out as follows: 30 cycles, 1 minute 94° C., 2 minutes 58° C., 50 seconds 72° C.

Example 17

Polymerase chain reaction (PCR) using PNA/DNA primer 1, 81-mer DNA matrix 3 and 9°N DNA polymerase™

The PCR is carried out as described in Example 16, but 9°N DNA polymerase is employed.

Reasonable variations, such as those which would occur to a skilled artisan, can be made herein without departing from the scope of the invention.

---

We claim:

1. A process for amplifying nucleic acids comprising:

obtaining a nucleic acid template;

hybridizing at least one PNA/DNA primer, each having at least one nucleoside unit with a 3'-hydroxyl group on the 3' end, to said nucleic acid template, to produce PNA/DNA primer-template hybrids; and amplifying linearly said PNA/DNA primer-template hybrid using at least one temperature-stable polymerase enzyme, wherein said temperature-stable polymerase enzyme is VENT™ polymerase, Pwo polymerase, TTH™ polymerase, or 9°N DNA POLYMERASE™, to produce linear amplification products.

2. A process for amplifying nucleic acids comprising:

obtaining a nucleic acid template;

hybridizing at least one PNA/DNA primer, each having one to three nucleoside units at the 3' end and at least one nucleoside unit with a 3'-hydroxyl group on the 3' end, to said nucleic acid template, to produce PNA/DNA primer-template hybrids; and amplifying linearly said PNA/DNA primer-template hybrid using at least one temperature-stable polymerase enzyme, to produce linear amplification products.

3. A process for amplifying nucleic acids comprising:

obtaining a nucleic acid template;

hybridizing at least one PNA/DNA primer, each having one nucleoside unit at the 3' end and at least one nucleoside unit with a 3'-hydroxyl group on the 3' end, to said nucleic acid template, to produce PNA/DNA primer-template hybrids; and amplifying linearly said PNA/DNA primer-template hybrid using at least one temperature-stable polymerase enzyme, to produce linear amplification products.

4. A process according to claim 1, wherein said temperature-stable polymerase enzyme comprises a combination of temperature-stable polymerase enzymes comprising VENT™ polymerase and TTH™ polymerase.

5. A method of diagnosing diseases comprising:

obtaining a nucleic acid template from a biological sample;

mixing at least one PNA/DNA primer, specific for diseases associated with the expression of one or more genes, and having at least one nucleoside unit with a 3'-hydroxyl group on the 3' end, with said nucleic acid template under conditons wherein specific hybridization would occur to produce PNA/DNA primer-template hybrids;

amplifying linearly said PNA/DNA primer-template hybrid using at least one temperature-stable polymerase enzyme, wherein said temperature-stable polymerase enzyme is VENT™ polymerase, Pwo polymerase, TTH™ polymerase, or 9° N DNA POLYMERASE™, to produce linearly amplified nucleic acid sequences; and diagnosing said diseases by detecting the presence, absence or the amount of linearly amplified nucleic acid sequences present in said biological sample.

6. The method of claim 5, wherein said temperature-stable polymerase enzyme comprises a combination of temperature-stable polymerase enzymes comprising VENT™ polymerase and TTH™ polymerase.

7. A method of diagnosing diseases comprising:

obtaining a nucleic acid template from a biological sample;

mixing at least one PNA/DNA primer, specific for diseases associated with the expression of one or more genes, and having one to three nucleoside units at the 3' end and at least one nucleoside unit with a 3'-hydroxyl group on the 3' end, with said nucleic acid template under conditions wherein specific hybridization would occur to produce PNA/DNA primer-template hybrids;

amplifying linearly said PNA/DNA primer-template hybrid using at least one temperature-stable polymerase enzyme to produce linearly amplified nucleic acid sequences; and diagnosing said diseases by detecting the presence, absence or the amount of linearly amplified nucleic acid sequences present in said biological sample.

8. A method of diagnosing diseases comprising:

obtaining a nucleic acid template from a biological sample;

mixing at least one PNA/DNA primer, specific for diseases associated with the expression of one or more genes, and having one nucleoside unit at the 3' end and at least one nucleoside unit with a 3'-hydroxyl group on the 3' end, with said nucleic acid template under conditions wherein specific hybridization would occur to produce PNA/DNA primer-template hybrids;

amplifying linearly said PNA/DNA primer-template hybrid using at least one temperature-stable polymerase enzyme to produce linearly amplified nucleic acid sequences; and diagnosing said diseases by detecting the presence, absence or the amount of linearly amplified nucleic acid sequences present in said biological sample.

* * * * *